(12) United States Patent
Liu

(10) Patent No.: US 9,592,188 B2
(45) Date of Patent: Mar. 14, 2017

(54) METHOD OF TREATING OR REDUCING THE SEVERITY OF DERMATOLOGICAL CONDITIONS

(71) Applicant: Yansong Liu, Derwood, MD (US)

(72) Inventor: Yansong Liu, Derwood, MD (US)

(*) Notice: Subject to any disclaimer, the term of this patent is extended or adjusted under 35 U.S.C. 154(b) by 0 days.

(21) Appl. No.: 14/718,979

(22) Filed: May 21, 2015

(65) Prior Publication Data

US 2015/0335562 A1    Nov. 26, 2015

Related U.S. Application Data

(60) Provisional application No. 62/001,727, filed on May 22, 2014.

(51) Int. Cl.
| | | |
|---|---|---|
| *A61K 31/365* | (2006.01) | |
| *A61Q 7/02* | (2006.01) | |
| *A61K 8/49* | (2006.01) | |
| *A61Q 19/00* | (2006.01) | |
| *A61K 9/00* | (2006.01) | |
| *A61Q 19/08* | (2006.01) | |

(52) U.S. Cl.
CPC .......... *A61K 8/4973* (2013.01); *A61K 9/0014* (2013.01); *A61K 31/365* (2013.01); *A61Q 7/02* (2013.01); *A61Q 19/00* (2013.01); *A61Q 19/004* (2013.01); *A61Q 19/007* (2013.01); *A61Q 19/08* (2013.01)

(58) Field of Classification Search
CPC .. A61K 8/4973; A61K 9/0014; A61K 31/365; A61Q 7/02; A61Q 19/00; A61Q 19/004; A61Q 19/007; A61Q 19/08

USPC ......................................................... 514/463
See application file for complete search history.

(56) References Cited

U.S. PATENT DOCUMENTS

| | | |
|---|---|---|
| 6,440,428 B1 | 8/2002 | Leander et al. |
| 6,932,983 B1 | 8/2005 | Straub et al. |
| 8,636,982 B2 | 1/2014 | Tamarkin et al. |
| 2003/0072814 A1 | 4/2003 | Maibach et al. |
| 2004/0214215 A1 | 10/2004 | Yu |
| 2006/0148728 A1 | 7/2006 | Lutz et al. |
| 2014/0030314 A1 | 1/2014 | Larson |

FOREIGN PATENT DOCUMENTS

| | | |
|---|---|---|
| EP | 0119852 | 9/1984 |
| WO | WO 9631207 | 10/1996 |
| WO | WO 0003708 | 1/2000 |
| WO | WO 0040269 | 7/2000 |
| WO | WO 2005007129 | 1/2005 |
| WO | WO 2006083979 | 8/2006 |
| WO | WO 2007070643 | 6/2007 |
| WO | WO 2008021981 | 2/2008 |
| WO | WO 2009083972 | 7/2009 |
| WO | WO 2011113000 | 9/2011 |

OTHER PUBLICATIONS

Hellberg et al. International journal of STD and AIDS, 1995, 6, 257-261.*

* cited by examiner

*Primary Examiner* — Yevegeny Valenrod
(74) *Attorney, Agent, or Firm* — Medler Ferro Woodhouse & Mills PLLC

(57) ABSTRACT

The present disclosure provides compositions and methods for treating dermatological disorders using a podophyllotoxin formulation.

18 Claims, 1 Drawing Sheet

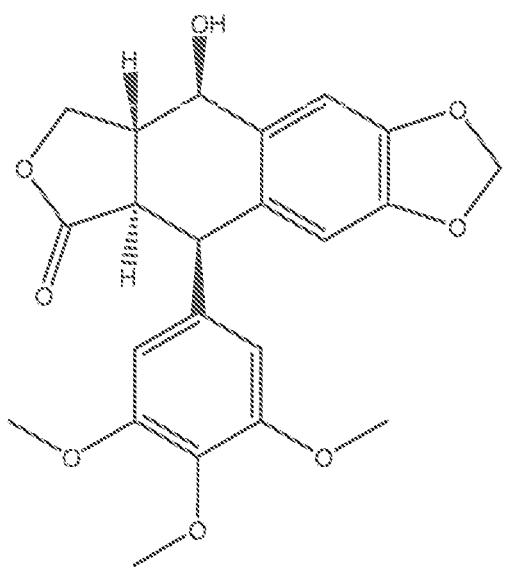
Podophyllotoxin

METHOD OF TREATING OR REDUCING THE SEVERITY OF DERMATOLOGICAL CONDITIONS

BACKGROUND OF THE INVENTION

This invention relates to topical compositions for treating skin and to methods of making and using the same.

Podophyllotoxin is a natural product extracted from the roots and rhizomes of certain *Podophyllum* species. Alternatively referred to as PPT or podofilox, podophyllotoxin has the structure shown in FIG. 1. Podophyllotoxin can also be prepared synthetically, as discussed in Reynolds, A., et al. "The Intramolecular Carboxyarylation Approach to Podophyllotoxin" *J. Am. Chem. Soc.,* 125(40): 12108-12109 (2003), the entirety of which is incorporated herein by reference.

Podophyllotoxin is biologically active and highly cytotoxic. It has been investigated as an oral anti-cancer agent and is also used as a precursor during the synthesis of anti-cancer agent Etoposide, a topoisomerase inhibitor. Podophyllotoxin is also FDA approved for the topical treatment of genital warts.

Although podophyllotoxin has been used as noted above, it has not achieved wide-spread use in the art generally, or been used in topical cosmetic applications, largely due to its well-known toxicity.

BRIEF SUMMARY OF THE INVENTION

Despite the paucity of uses for podophyllotoxin, it has now been surprisingly discovered that, despite its toxicity, many dermatological conditions, such as fine lines, wrinkles, dry skin, excessive pore size, skin dyschromia, reduced, elasticity, unwanted hair, skin thinning, purpura, actinic keratosis, pruritus (itching), eczema, acne, rosacea, erythema (redness), telangiectasia, (spider veins), skin cancer (including basal cell carcinoma, squamous cell carcinoma, and melanoma), sunburn, dermatitis, rashes, impetigo, rhinophyma, perioral dermatitis, pseudofolliculitis barbae (barber's itch), erythema multiforme (a hypersensitivity reaction), erythema nodosum, granuloma annulare, alopecia, ichthyosis vulgaris, fungal infections, herpes simplex, keloids, milia, moluscum contagiosum, urticarial (hives), vascular tumors and malformations, as well as combinations thereof can be treated via the topical administration of an effective amount of a formulation comprising from about 0.001 to about 0.5 wt % podophyllotoxin, for a period of time sufficient to reduce the severty of the dermatological condition.

In a particular embodiment, the present disclosure provides a method of treating dermatological conditions in a subject in need thereof, comprising topically administering to a skin surface of the subject an effective amount of a formulation comprising from about 0.001 to about 0.5 wt % podophyllotoxin or a podophyllotoxin derivative, for a period of time sufficient to reduce the severity of the dermatological condition.

In certain embodiments, the dermatological condition is selected from the group consisting of fine lines, wrinkles, dry skin, excessive pore size, skin dyschromia, reduced elasticity, unwanted hair, skin thinning, purpura, actinic keratosis, pruritus, eczema, acne, rosacea, erythema, telangiectasia, skin cancer, sunburn, dermatitis, rashes, impetigo, rhinophyma, perioral dermatitis, pseudofolliculitis barbae, erythema multiforme, erythema nodosum, granuloma annulare, alopecia, ichthyosis vulgaris, fungal infections, herpes simplex, keloids, milia, moluscum contagiosum, urticarial, vascular tumors and malformations, and combinations thereof.

In certain embodiments, the period of time is from about 1 to about 52 weeks.

In other embodiments, the period of time is from about 1 to about 36 weeks.

In still further embodiments, the period of time is from about 1 to about 18 weeks.

In yet another embodiment, the period of time is from about 1 to about 12 weeks, In another embodiment, the period of rime is less than about 12 weeks.

In certain embodiments, the skin surface is selected from the group consisting of a facial surface, hands, arms, legs, stomach, décolletage, feet, and combinations thereof.

In certain embodiments, the skin surface is a facial surface.

In certain embodiments, the facial surface is a forehead, a perioral surface, a chin surface, a periorbital surface, a nasal surface, a cheek skin surface, or a combination thereof.

In certain embodiments, the reduction of the dermatological condition is measured using Rapid Evaluation of Antiaging Leads (REAL 3.0) system.

In certain embodiments, the reduction of the dermatological condition is statistically significant.

In certain embodiments, the podophyllotoxin formulation comprises at least one fat selected from the group consisting of lard, butter, palm oil, shea butter, mango butter, kokurn butter, cocoa butter, decanoic acid, undecanoic acid, erucic acid, tetradeconol, tridecanal, lauryl alcohol, beneicosane, mono decane, octadecane, ercosane, elemi resin, levulinic acid, coconut oil, dimethyl sebacate, adipic acid, polyethylene glycol, diethylene glycol, monotetradecyl ether, diethylene glycol, heptaethycine glycol monododecyl ether, palmitate esters, stearate esters, polycaprolactone-block-polytetrahydro-furan-block-poly[di(ethyleneglycol)adipate], hydrogenated oils, squalane, petroleum, solid paraffin, carnuba wax, bees wax, lanolin, trilaurin, stearic acid, palmitic acid, capric acid, myristic acid, lauric acid, tallow, whale blubber, and combinations thereof.

In some embodiments, the fatty substance is selected from the group consisting of shea butter, mango butter, kokum butter, cocoa butter, and combinations thereof.

The method of claim 1, wherein site podophyllotoxin formulation is an emulsion.

The method of claim 15, wherein the emulsion is an oil in water emulsion.

The method of claim 15, wherein the emulsion is a water in oil emulsion.

The method of claim 1, wherein the podophyllotoxin formulation comprises a siloxane.

The method of claim 18, wherein the siloxane is a cyclic siloxane.

The method of claim 19, wherein the cyclic siloxane is selected from the group consisting of cyclotetrasiloxane, cyclopentasiloxane (cyclomethicone), cyclohexasiloxane, and combinations thereof.

BRIEF DESCRIPTION OF THE DRAWINGS/FIGURES

The foregoing summary, as well as the following detailed description of the embodiments, will be better understood when read in conjunction with the appended figures. For the purpose of illustration, the figures may describe the use of specific embodiments. It should be understood, however, that the integrated processes described herein are not limited to the precise embodiments discussed or described in the figures.

FIG. 1 is the structure of podophyllotoxin.

DETAILED DESCRIPTION OF THE INVENTION

The articles "a", "an," and "the" are used herein to refer to one or to more than one (i.e., to at least one) of the grammatical object of the article. By way of example, "an element" means one element or more than one element.

As used herein, the phrase "podophyllotoxin derivative" includes, but is not limited to known podophyllotoxin derivatives, including those podophyllotoxin derivatives disclosed in, for example, in Z.-J. Zhang et al. "Design, synthesis and cytotoxic activity of novel sulfonylurea derivatives of podophyllotoxin" *Bioorg. Med, Chem,* 22:204-210 (2014) and You, Youngjae, "Podophyllotoxin Derivatives: Current Synthetic Approaches for New Anti-cancer Agents," *Current Pharmaceutical Design* 11.13: 1695-1717 (2005), each of which is incorporated herein by reference in its entirety.

The present disclosure provides a method of treating dermatological conditions comprising topically administering to a subject in need thereof an effective amount of a formulation comprising from about 0.001 to about 0.5 wt % podophyllotoxin or a podophyllotoxin derivative, for a period of time sufficient to reduce the severity of the dermatological condition. In particular embodiments, the formulation can comprise about 0.001 weight % podophyllotoxin, about 0.01 weight % podophyllotoxin, about 0.1 weight % podophyllotoxin, about 0.25 weight % podophyllotoxin, or about 0.5 weight % podophyllotoxin.

The formulations described herein can be substantially free of mercury, lead, and/or hormones. As used herein, the phrase "substantially fee" with respect to mercury and lead means, not more than the quantities of these materials permitted by the FDA, For example, in certain embodiments, the formulations herein contain less than about 1 PPM mercury and less than about 20 PPM lead. With respect to hormones, the phrase "substantially free" means not more than about 100 PPM, not more than about 50 PPM, not more than about 10 PPM, not more than about 1 PPM, not more than about 0.1 PPM, cot more than about 0.001 PPM, or not more than about 0.0001 PPM of any given hormone or combination of hormones.

In certain embodiments, the dermatological condition can be fine uses, wrinkles, dry skin, excessive pore size, skin dyschromia, reduced elasticity, unwanted hair, skin thinning, purpura, actinic keratosis, pruritus (itching), eczema, acne, rosacea, erythema (redness), telangiectasia (spider veins), skin cancer (including basal cell carcinoma, squamous cell carcinoma, and melanoma), sunburn, dermatitis, rashes, impetigo, rhinophyma, perioral dermatitis, pseudofolliculitis barbae (barber's itch), erythema multiforme (a hypersensitivity reaction), erythema nodosum, granuloma annulare, alopecia, ichthyosis vulgaris, fungal infections, herpes simplex, keloids, mills, moluscum contagiosum, urticarial (hives), vascular tumors and malformations, as well as combinations thereof. It is understood that, for purposes of the present disclosure, dermatological conditions do not include psoriasis or genital warts (condyloma acuminata).

While many of the dermatological conditions described herein can occur at any age, many are also age-related skin conditions that become more pronounced with age. exposure to harsh environments (including UV exposure, wind, cold, dry climate, etc.), or a combination of both. Exemplary age-related skin conditions include, but are not limited to, fine lines, wrinkles, dry skin, excessive pore size, skin dyschromia, reduced elasticity, unwanted hair, skin thinning, purpura, actinic keratosis, pruritus, eczema, acne, rosacea, erythema, telangiectasia, actinic telangiectasia, skin cancer, and rhinophyma.

Without wishing to be bound by any particular theory, tine lines and wrinkles are believed to arise because of a breakdown of collagen and elastin in the skin caused and/or exacerbated by exposure to harmful UV radiation.

Dry skin is associated with itching, burning, and cracking of the epidermis. Dry skin can have many causative factors including, but not limited to, wind, extreme temperatures (both hot and cold), and air-conditioning, all of which cause the skin to lose moisture.

Although pore size is determined, to a certain extent, by genetics—pores can become larger with age or repeated sun exposure. Pores can also appear larger and more noticeable when clogged with dirt, oil and/or dead skin cells.

Skin dyschromias are discolorations (either lightening or darkening) of the epidermis. Although there axe many known dyschromias, exemplary dyschromias suitable tor treatment with the formulations described herein include post-inflammatory hyperpigmentation (PIH) and melasma.

Reduced elasticity in skin is often associated with changes in the connective tissue that reduce the skin's strength and elasticity. Reduced elasticity is especially pronounced after prolonged sun-exposure. Common features of reduced skin elasticity include the leathery, weather-beaten appearance common to those individuals who spend a large amount of time outdoors.

Purpura is the appearance of red or purple discolorations on the skin that do not blanch on applying pressure. The discolorations associated with purpura are caused by bleeding underneath the skin usually secondary to vasculitis or dietary deficiency of vitamin C (scurvy). They are also common in older individuals (senile purpura).

Actinic keratosis is a premalignant condition associated with photo-damaged skin. Actinic keratoses, also called AKs (they rarely appear alone) typically appear on sun-exposed areas such as the face, scalp, lips, and the hack of the hands. AKs are often elevated, rough in texture, and resemble warts. Untreated AKs can advance to squamous cell carcinoma (SCC).

Eczema is inflammation of the skin, characterized by itchy, erythematous, vesicular, weeping, and crusting patches. Although the etiology of eczema is not well understood, it is believed to have an autoimmune component.

Rosacea is a chronic skin condition characterized by redness of the facial skin. Of the four known subtypes, the formulations described herein are suitable for treating erythematotelangiectatic rosacea, papulopustular rosacea, and phymatous rosacea.

Impetigo is a highly contagious skin disease common among school children. Impetigo usually appears as red sores on the face, especially around a child's nose and mouth. The sores burst and develop honey-colored crusts.

Rhinophyma is a large, bulbous, ruddy nose caused by granulomatous infiltration, commonly due to untreated phymatous rosacea.

Perioral dermatitis is skin disease characterized by multiple small papules, pustules, and vesicles which are localized in and around the perioral skin, nasolabial folds, or perioccular area.

Erythema nodosum (EN) is an inflammatory condition characterized by inflammation of fat cells under the skin, resulting in tender red nodules or lumps on the shins, buttocks, calves, ankles, thighs, and/or arms.

Granuloma annulare is a skin condition that most commonly consists of raised, reddish or skin-colored lesions that form ring patterns—usually on the backs of the forearms, hands, and/or feet. Sometimes the lesions may burn or itch. The lesions are caused by the clustering off cells below the skin.

Ichthyosis vulgaris is a genetic skin disorder causing dry, scaly skin.

A keloid is the result of an overgrowth of granulation tissue (collagen type 3) at the site of a healed skin injury which is then slowly replaced by collagen type 1. Keloids are firm, rubbery lesions or shiny, fibrous nodules, and can vary in shape and color, Milia are small white bumps or cysts on the skin almost always observed in newborn babies.

moluscum contagiosum is a viral infection of the skin or mucous membrane. It is caused by a DNA poxvirus called the molluscum contagiosum virus (MCV).

In particular embodiments, the formulation can be a topically acceptable formulation, including, but not limited to an emulsion (such as a lotion, cream, shampoo, etc.), a wax, a gel, an oil, or a foam. Emulsions can be oil in water emulsions or water in oil emulsions, many examples of which are known in the art. In a particular embodiment, the formulation can be a water in oil emulsion.

When the formulation is a water in oil emulsion, the formulation can comprise from about 1 to about 30 weight percent water. In other embodiments, the formulation can comprise from about 40 to about 80 weight percent water. In other embodiments, the formulation can comprise from about 60 to about 90 weight percent.

In some embodiments, the podophyllotoxin or podophyllotoxin derivative can be completely suspended in the formulation. In other embodiments, it can be completely soluble in the formulation. And in still other embodiments, a portion of the podophyllotoxin or podophyllotoxin derivative in the formulation can be suspended while the remainder of the podophyllotoxin or podophyllotoxin derivative can be solubilized. In particular embodiments, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99% of the podophyllotoxin can be suspended in the formulation.

In embodiments, wherein some amount of the podophyllotoxin or podophyllotoxin derivative is suspended in the formulation, it can be suspended uniformly. That is, the suspended podophyllotoxin or podophyllotoxin derivative will be dispersed evenly throughout the formulation such that separate aliquots of the formulation taken from different locations within the same batch will have substantially similar concentration of the suspended podophyllotoxin or podophyllotoxin derivative.

In addition to podophyllotoxin (or a podophyllotoxin derivative) and water, the formulation suitable for use in the present method can also include other ingredients commonly used in skin care and hair care products such as antimicrobials, anti-inflammatories, moisturizers, waxy alcohols, hydration agents, penetration agents, emulsifiers, natural or synthetic oils, solvents, fats, surfactants, detergents, gelling agents, emollients, antioxidants, fragrances, fillers, thickeners, waxes, odor absorbers, dyestuff, coloring agents, powders, viscosity-controlling agents, anesthetics, anti-itch agents, botanical extracts, conditioning agents, darkening or lightening agents, glitter, hair pigment additives, humectants, mica, minerals, polyphenols, silicones or silicone derivatives, sun blocks, vitamins, phytomedicinals, and other compounds as listed in the International Cosmetic Ingredient Dictionary and Handbook, 13th Ed. (2009), the entirety of which is incorporated herein by reference.

In certain embodiments, the formulation can further include a hyaluronic acid derivative, such as a hyaluronin oligosaccharide. Without wishing to be bound to any particular theory, it is believed that hyaluronin oligosaccharides, when present, work synergistically with the podophyllotoxin. In particular embodiments, the hyaluronin oligosaccharides can have a molecular weight of from about 500 to less than about 50,000 daltons. In particular embodiments, the hyaluronin oligosaccharides can have a molecular weight of from about 500 to about 25,000 daltons. And in still further embodiments, the hyaluronin oligosaccharides can have a molecular weight of from about 500 to about 12,500 daltons. Exemplary hyaluronin oligosaccharides, and methods of making them, are disclosed in U.S. Published Application No. 2010/0098794, the entirety of which is incorporated herein by reference.

Exemplary antimicrobials suitable for use in the formulations described herein include, but are not limited to, phenoxyethanol, methylparaben, ethylparaben, propylparaben, butylparaben, and combinations thereof. In a particular embodiment, the formulation described herein can comprise a combination of methylparaben and ethylparaben. In other embodiments, the formulation can comprise propylparaben and/or phenoxyethanol.

Exemplary antioxidants suitable for use in the formulations described herein include, but are not limited to, butylatedhydroxytoulene (BHT) and butylatedhydroxyanisole (BHA).

Exemplary waxy alcohols suitable for use in the formulations described herein include, but are not limited to, those alcohols having from fourteen carbon atoms to thirty carbon atoms, examples of which include octadecanol, stearyl alcohol, n-heptadecanol, and nonadecyl alcohol. In particular embodiments, the formulation can comprise octadeanol. In other embodiments, the formulation can comprise stearyl alcohol. In still further embodiments, the formulation can comprise n-heptadecanol.

Exemplary fats suitable for use in the formulations described herein include, but are not limited to, lard, butter, palm oil, shea butter, mango butter, kokum butter, cocoa butter, decanoic acid, undecanoic acid, erucic acid, tetradeconol, tridecanol, lauryl alcohol, beneicosane, mono decane, octadecane, ercosane, elemi resin, levulinic acid, coconut oil, dimethyl sebacate, adipic acid, polyethylene glycol, diethylene glycol, monotetradecyl ether, diethylene glycol, heptaethycine glycol monododecyl ether, palmitate esters, stearate esters, polycaprolactone-block-polytetrahydrofuran-block-poly[di(ethyleneglycol)adipate], hydrogenated oils, squalane, petroleum, solid paraffin, carnuba wax, bees wax, lanolin, trilaurin, stearic acid, palmitic acid, capric acid, myristic acid, lauric acid, tallow, whale blubber, and combinations thereof.

In a particular embodiment, the formulation described herein can comprise cocoa butter. In other embodiments, the formulation can comprise shea butter. In still further embodiments, the formulation can comprise & combination of shea buster and cocoa butter.

Exemplary emulsifiers suitable for use in the formulations described herein include, but are not limited to, glyceryl stearate, glyceryl monooleate, PEG stearates (such as, but not limited to, PEG-100 stearate, PEG-200 stearate, PEG- 300 stearate, etc.), sorbitan sesquistearate, sorbitan olivate, sorbitan stearate, lecithin, undeceth-3, PEG-20 methyl glucose sesquistearate, trideceth-3, trideceth-12, laureth-9, behenoyl stearic acid, oleth-2, oleth-20, sorbitan laurate, sorbitan palmitate, sorbitan oleate, sorbitan trioleate, steareth-2, steareth-20, steareth-21, laureth-23, C11-15-Pareth-15, PPG-24-buteth-27, Avena sativa (oat) peptides, high molecular weight polymers of ethylene oxide and propylene oxide, PPG-5-ceteth-10 phosphate, oleth-5 phosphate, dioleyl phosphate, oleth-3 phosphate, oleth-10 phosphate, lauryl phosphate, trideceth-3 phosphate, trideceth-6 phosphate, deceth-6 phosphate, trilaureth-4 phosphate, C20-22 alkyl phosphate, C20-22 Alcohols, polyglyceryl-10 decaoleate, polyglyceryl-3 oleate, PEG/PPG-20/6 dimethicone, bis-PEG/PPG-20/20 dimethicone, bis-PEG/PPG-16/16 PEG/PPG-16/16 dimethicone, bis-PEG/PPG-20/5 PEG/PPG-20/5 dimethicone, methoxy PEG/PPG-25/4 dimethicone, bis-PEG/PPG-14/14 dimethicone, PEG-11 methyl ether dimethicone, PEG/PPG-20/22 butyl ether dimethicone, lauryl PEG-9 polydimethylsiloxyethyl dimethicone, PEG-10 dimethicone, polyglyceryl-3 disiloxane dimethicone, lauryl polyglyceryl-3 polydimethylsiloxyethyl dimethicone, lauryl PEG-8 dimethicone, sodium stearate, sucrose laurate, sucrose myristate, sucrose stearate, methyl mlucose sesquistearate, and combinations thereof.

In particular embodiments, the emulsifier can be a PEG-stearate. In other embodiments, the emulsifier can be PEG-100 stearate. In still other embodiments, the emulsifier can be a mixture of PEG-100 stearate and second emulsifier. In certain embodiments, the second emulsifier can be Avena sativa (oat) peptides. Without wishing to be bound by any particular theory, it is believed that oat peptide enhances skin's elasticity, promotes skin metabolism, and helps skin retain its moisture. Oat peptide is available from a variety of companies, including, for example, Shenyang Jihua Material Ltd. (China).

Exemplary natural and synthetic oils suitable for use in the formulations described herein include, but are not limited to, liquid paraffin, jojoba oil, grape seed oil, coconut oil, olive oil, castor oil, cottonseed oil, wheat germ oil, sunflower oil, safflower oil, carrot seed oil, and combinations thereof. In particular embodiments, the formulation can comprise jojoba oil. In other embodiments, the formulation can comprise grape seed oil. In certain embodiments, the formulation can comprise liquid paraffin in combination with at least a second oil. In particular embodiments, the second oil can be jojoba oil.

Exemplary emollients suitable for use in the formulations described herein include, but are not limited to, Isocetyl Palmitate (WAGLINOL 24416), Isocetyl Stearate (LASEMUL 244), Isodecyl Oleate (WEICHOL 158), Isononyl Isononanoate (WAGLINOL 1449), Isononyl Isononanoate (WAGLINOL 1449 NF), Isopropyl isostearate (SOLDOC 60), Isopropyl Myristate (WAGLINOL 6014), Isopropyl Myristate/Isopropyl Palmitate (WAGLINOL 6014/16), Isopropyl Palmitate (WAGLINOL 6016), Isopropyl Stearate (LASEMUL 60), Isostearyl isostearate (SOLDOC 272), Isotridecyl Isononanoate (WAGLINOL ITD 9), Myristyl Miristate (WAGLINOL 21414), Neopentyl Glycol Diethythexanoate (WAGLINOL 2/1048), Neopentyl Glycol Diheptanoate (WAGLINOL 2/10407), and Octyldodecyl Myristate (WAGLINOL 30014). In a particular embodiment, the emollient is Isononyl Isononanoate (WAGLINOL 1449 NF).

Exemplary humectants suitable for use in the formulations described herein include, but are not limited to, glycerol, sorbitol, alkylene glycols (e.g., propylene glycol, dipropylene glycol, polypropylene glycol, polyethylene glycol, hexylene glycol, butylene glycol, 1,3-butylene glycol, etc.), C1-3 alkoxylated glucose derivatives, glyceryl triacetate, hexanetriol, vinyl alcohol, xylitol, Maltitol polydextrose, alkoxylated glycerin (like ethoxylated glycerin), quillaia, urea, aloe vera gel, MP Diol (also known as 2-methyl-1,3-propane diol), alpha hydroxy acids (e.g., lactic acid), honey and combinations thereof. In particular embodiments, the formulation herein can comprise glycerol, sorbitol, propylene glycol, hexylene glycol, or a combination thereof.

Exemplary anti-inflammatories suitable for use in the formulations described herein include, but are not limited to, botanically-derived compounds, such as allantoin, witch hazel, aloe vera, chamomile, thyme extract, echinacea, purslane extract, or combinations thereof. In particular embodiments, the formulation described herein can comprise allantoin.

Exemplary silicones or silicone derivatives suitable for use in the formulations described herein can be siloxanes. In some embodiments, the siloxanes can be cyclic siloxanes. In certain embodiments, the cyclic siloxanes can be cyclotetrasiloxane, cyclopentasiloxane (cyclomethicone), cyclohexasiloxane, and combinations thereof. In some embodiments, the formulation described herein can include at least one cyclic siloxane. In other embodiments, the cyclic siloxane can be cyclomethicone or cyclotetrasiloxane.

In certain embodiments, the formulation described herein can Include one or more pH adjusting agents. Suitable pH adjusting agents are known to those of ordinary skill in the art and include any pharmaceutically acceptable acid or base. In certain embodiments, though, the formulation described herein can be substantially free of any pH adjusting agents.

The formulation described herein can have a pH in the range of about 5 to about 7.5, and in certain embodiments, about 5 to about 7, about 6 to about 7, from about 6.1 to about 6.8, or from about 6.4 to about 6.6.

Although the period of time sufficient to reduce the severity of the dermatological conditions discussed herein will vary depending upon the patient, the dermatological condition itself, and the concentration of the podophyllotoxin in the formulation topically administered to the subject, in certain embodiments, the period of time sufficient to reduce the severity of the dermatological condition can be for examples about 52 weeks, about 36 weeks, about 26 weeks, about 18 weeks, about 16 weeks, about 15 weeks, about 14 weeks, about 13 weeks, about 12 weeks, about 11 weeks, about 10 weeks, about 9 weeks, about 8 weeks, about 7 weeks, about 6 weeks, about 5 weeks, about 4 weeks, about 3 weeks, about 2 weeks, or about 1 week.

The formulation described herein cart be applied, for example, once daily, twice daily, three times daily, four time daily, or five times daily, for any of the periods of time noted above. In alternative embodiments, the formulation described herein can be applied once, twice, three time, four times, or five times a day every other day, every third day, every fourth day, every fifth day, every sixth day, or once a week for the periods of time noted above. For example, and without limitation, the formulation can be applied once a day every day, once a day every other day, twice a day every third day, once a day one time a week, etc.

The formulation described herein can be applied to any body surface, including, but not limited to, a facial surface, the scalp, neck, ears, shoulders, chest (including breasts and/or the décolletage), arms, hands, legs, stomach, buttocks, groin, back, feet, and combinations thereof. In particular embodiments, the facial surface can be the forehead, a perioral surface, a chin surface, a periorbital surface, a nasal surface, a cheek skin surface, or a combination thereof. A given body surface can be afflicted with one or more of the dermatological conditions described herein and more than one body surface can be treated at a time.

Effectiveness of the formulation for reducing the severity of the dermatological conditions can be measured using, for example, expert visual grading of high-resolution digital images taken at baseline (i.e., prior to treatment) and at other predetermined time points using the Rapid Evaluation of Anti-aging Leads ("REAL" 3.0) system. The REAL system and its use are described in "A randomized, controlled comparative study of the wrinkle reduction benefits . . . " J. J. J. Fu et al., *British Journal of Dermatology*, 162:647-654 (2010), the entirety of which is incorporated herein by reference.

According to the described method, three trained expert graders independently assess changes in the appearance of a given skin surface by comparing identified baseline and post-treatment images at given time points side-by-side using a ± eight-point ordinal scale. The expert graders and other assessors are blinded to tire treatments. Although Fu et al used 8 and 24 weeks as the time points for comparison, other time points can be used as appropriate for a given dermatological condition. Similarly, although Fu et al, describes the use of expert graders, grading can be performed by computer.

The formulations described herein can be prepared according to known procedures. In a particular embodiment, a formulation described herein can be prepared by dissolving podophyllotoxin or a podophyllotoxin derivative in stearyl alcohol or other appropriate solvent to give a solution. A base, comprising a mixture of the various elements disclosed herein can then be prepared at a temperature in the range of from about 40° C. to about 90° C., and in certain embodiments, at about 65° C. or at about 75° C. The solution can then be carefully added to the base with mixing to give the formulation described herein.

The phraseology or terminology herein is for the purpose of description and not of limitation. As such, the terminology and/or phraseology of the present specification should be interpreted by the skilled artisan in light of the teachings and guidance herein.

The breadth and scope of the present Invention should not be limited by any of the above-described exemplary embodiments, but should be defined only in accordance with the following claims and their equivalents.

What is claimed is:

1. A method of treating a dermatological condition selected from the group consisting of fine lines, wrinkles, dry skin, excessive pore size, skin dyschromia, reduced elasticity, skin thinning, actinic keratosis, pruritus, eczema, acne, sunburn, dermatitis, pseudofolliculitis barbae, and combinations thereof in a subject in need thereof, comprising topically administering to a skin surface of the subject an effective amount of a formulation comprising from about 0.001 to about 0.1 wt % podophyllotoxin, for a period of time sufficient to reduce the severity of the dermatological condition.

2. The method of claim 1, wherein the period of time is from about 1 to about 52 weeks.

3. The method of claim 2, wherein the period of time is from about 1 to about 36 weeks.

4. The method of claim 3, wherein the period of time is from about 1 to about 18 weeks.

5. The method of claim 4, wherein the period of time is from about 1 to about 12 weeks.

6. The method of claim 4, wherein the period of time is less than about 12 weeks.

7. The method of claim 1, wherein the skin surface is selected from the group consisting of a facial surface, hands, arms, legs, stomach, decolletage, feet, and combinations thereof.

8. The method of claim 7, wherein the skin surface is a facial surface.

9. The method of claim 8, wherein the facial surface is a forehead, a perioral surface, a chin surface, a periorbital surface, a nasal surface, a cheek skin surface, or a combination thereof.

10. The method of claim 1, wherein the reduction of the dermatological condition is statistically significant.

11. The method of claim 1, wherein the formulation comprises at least one fat selected from the group consisting of lard, butter, palm oil, shea butter, mango butter, kokum butter, cocoa butter, decanoic acid, undecanoic acid, erucic acid, tetradeconol, tridecanal, lauryl alcohol, beneicosane, mono decane, octadecane, ercosane, elemi resin, levulinic acid, coconut oil, dimethyl sebacate, adipic acid, polyethylene glycol, diethylene glycol, monotetradecyl ether, diethylene glycol, heptaethycine glycol monododecyl ether, palmitate esters, stearate esters, polycaprolactone-block-polytetrahydro-furan-blockpoly[di(ethyleneglycol)adipate], hydrogenated oils, squalane, petroleum, solid paraffin, camuba wax, bees wax, lanolin, trilaurin, stearic acid, palmitic acid, capric acid, myristic acid, lauric acid, tallow, whale blubber, and combinations thereof.

12. The method of claim 11, wherein the at least one fat is selected from the group consisting of shea butter, mango butter, kokum butter, cocoa butter, and combinations thereof.

13. The method of claim 1, wherein the formulation is an emulsion.

14. The method of claim 13, wherein the emulsion is an oil in water emulsion.

15. The method of claim 13, wherein the emulsion is a water in oil emulsion.

16. The method of claim 1, wherein the podophyllotoxin formulation comprises a siloxane.

17. The method of claim 16, wherein the siloxane is a cyclic siloxane.

18. The method of claim 17, wherein the cyclic siloxane is selected from the group consisting of cyclotetrasiloxane, cyclopentasiloxane (cyclomethicone), cyclohexasiloxane, and combinations thereof.

* * * * *